United States Patent
Brunner et al.

(10) Patent No.: US 7,604,623 B2
(45) Date of Patent: Oct. 20, 2009

(54) FLUID APPLICATOR WITH A PRESS ACTIVATED POUCH

(75) Inventors: Michael S. Brunner, Roswell, GA (US); Cecelia M. Berger Sharp, Atlanta, GA (US); Tamara L. Mace, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 409 days.

(21) Appl. No.: 11/215,816

(22) Filed: Aug. 30, 2005

(65) Prior Publication Data

US 2007/0048062 A1    Mar. 1, 2007

(51) Int. Cl.
*A61F 13/15* (2006.01)
*A61F 13/20* (2006.01)

(52) U.S. Cl. .................. 604/385.101; 604/383; 604/385.11; 604/385.19

(58) Field of Classification Search .......... 604/358, 604/367, 385.01, 385.101, 383, 385.11, 385.19; D9/723; 222/92–96, 526–527, 531–532, 222/541.1–541.4; 401/6–7
See application file for complete search history.

(56) References Cited

U.S. PATENT DOCUMENTS

| | | | |
|---|---|---|---|
| 1,941,320 A * | 12/1933 | Pamplin | 401/7 |
| 2,173,528 A * | 9/1939 | Beale | 422/292 |
| 2,790,982 A * | 5/1957 | Schneider | 401/7 |
| 2,980,940 A | 4/1961 | Crowe | |
| 3,299,464 A | 1/1967 | O'Brien et al. | |
| 3,338,992 A | 8/1967 | Kinney | |
| 3,341,394 A | 9/1967 | Kinney | |
| 3,386,793 A | 6/1968 | Stanton | |
| 3,481,676 A | 12/1969 | Schwartzman | |
| 3,485,562 A | 12/1969 | Hidden et al. | |
| 3,494,821 A | 2/1970 | Evans | |
| 3,502,538 A | 3/1970 | Petersen | |
| 3,502,763 A | 3/1970 | Hartmann | |
| 3,542,615 A | 11/1970 | Dobo et al. | |
| 3,608,708 A * | 9/1971 | Storandt | 206/361 |
| 3,640,877 A | 2/1972 | Gobert | |
| 3,692,618 A | 9/1972 | Dorschner et al. | |
| 3,722,174 A | 3/1973 | Bergevin et al. | |

(Continued)

FOREIGN PATENT DOCUMENTS

DE        3335614        4/1985

(Continued)

OTHER PUBLICATIONS

Co-pending U.S. Appl. No. 10/844,568, filed Apr. 30, 2004.

(Continued)

*Primary Examiner*—Michele Kidwell
(74) *Attorney, Agent, or Firm*—Dority & Manning, P.A.

(57) ABSTRACT

A fluid applicator device includes a cover layer and a pouch positioned adjacent a back side of said cover layer. A fluid composition is contained within the pouch. Exit structure is configured at a location on the pouch and is adjacent to the cover layer. The exit structure is in isolated fluid communication with a defined portion of the cover layer that is permeable to the fluid composition within the defined portion such that the fluid composition released from the pouch migrates through the cover layer only within the defined portion.

29 Claims, 4 Drawing Sheets

U.S. PATENT DOCUMENTS

| | | | |
|---|---|---|---|
| 3,768,916 A | 10/1973 | Avery | |
| 3,802,817 A | 4/1974 | Matsuki et al. | |
| 3,826,259 A * | 7/1974 | Bailey | 604/310 |
| 3,849,241 A | 11/1974 | Butin et al. | |
| 3,855,046 A | 12/1974 | Hansen et al. | |
| 3,998,559 A | 12/1976 | Hoyt | |
| 4,027,985 A | 6/1977 | Loesser, III | |
| 4,058,425 A * | 11/1977 | Thrun | 156/200 |
| 4,084,910 A | 4/1978 | LaRosa | |
| 4,100,324 A | 7/1978 | Anderson et al. | |
| 4,144,370 A | 3/1979 | Boulton | |
| 4,148,318 A | 4/1979 | Meyer | |
| 4,291,697 A | 9/1981 | Georgevich | |
| 4,318,818 A | 3/1982 | Letton et al. | |
| 4,330,220 A | 5/1982 | Schaar et al. | |
| 4,340,563 A | 7/1982 | Appel et al. | |
| 4,415,288 A | 11/1983 | Gordon et al. | |
| 4,430,013 A | 2/1984 | Kaufman | |
| 4,469,463 A | 9/1984 | Van Overloop | |
| 4,475,835 A | 10/1984 | Verboom et al. | |
| 4,478,530 A | 10/1984 | Van Overloop | |
| 4,525,091 A | 6/1985 | Van Overloop | |
| 4,526,773 A | 7/1985 | Weber | |
| 4,545,180 A | 10/1985 | Chung et al. | |
| 4,563,103 A | 1/1986 | Van Overloop et al. | |
| 4,576,817 A | 3/1986 | Montgomery et al. | |
| 4,578,265 A | 3/1986 | Pellico et al. | |
| 4,596,481 A * | 6/1986 | Tanaka | 401/132 |
| 4,638,913 A | 1/1987 | Howe, Jr. | |
| 4,657,802 A | 4/1987 | Morman | |
| 4,659,609 A | 4/1987 | Lamers et al. | |
| D290,292 S | 6/1987 | Gatarz | |
| 4,784,506 A | 11/1988 | Koreska et al. | |
| 4,805,767 A | 2/1989 | Newman | |
| 4,818,464 A | 4/1989 | Lau | |
| 4,828,556 A | 5/1989 | Braun et al. | |
| 4,833,003 A | 5/1989 | Win et al. | |
| 4,885,155 A | 12/1989 | Parran, Jr. et al. | |
| 4,948,427 A | 8/1990 | Yamagishi et al. | |
| 4,978,232 A | 12/1990 | Dunton | |
| 5,048,589 A | 9/1991 | Cook et al. | |
| 5,059,035 A | 10/1991 | Kristensen | |
| 5,090,832 A | 2/1992 | Rivera et al. | |
| 5,094,559 A | 3/1992 | Rivera et al. | |
| 5,169,251 A | 12/1992 | Davis | |
| 5,270,337 A | 12/1993 | Graf | |
| 5,273,514 A | 12/1993 | Kristensen | |
| 5,284,703 A | 2/1994 | Everhart et al. | |
| 5,284,871 A | 2/1994 | Graf | |
| 5,348,943 A | 9/1994 | Pickart | |
| 5,350,624 A | 9/1994 | Georger et al. | |
| 5,382,400 A | 1/1995 | Pike et al. | |
| 5,399,412 A | 3/1995 | Sudall et al. | |
| 5,510,001 A | 4/1996 | Hermans et al. | |
| 5,591,309 A | 1/1997 | Rugowski et al. | |
| 5,591,510 A | 1/1997 | Junker et al. | |
| 5,620,779 A | 4/1997 | Levy et al. | |
| 5,637,194 A | 6/1997 | Ampulski et al. | |
| 5,654,164 A | 8/1997 | Gardiol et al. | |
| 5,695,868 A | 12/1997 | McCormack | |
| D390,708 S | 2/1998 | Brown | |
| 5,772,845 A | 6/1998 | Farrington, Jr. et al. | |
| 5,791,801 A | 8/1998 | Miller | |
| 5,792,213 A | 8/1998 | Bowen | |
| 5,804,401 A | 9/1998 | Gardiol et al. | |
| 5,843,056 A | 12/1998 | Good et al. | |
| 5,891,422 A | 4/1999 | Pan et al. | |
| 5,911,915 A | 6/1999 | Fonsny et al. | |
| 5,916,862 A | 6/1999 | Morelli et al. | |
| 5,942,482 A | 8/1999 | Zocchi et al. | |
| 5,962,112 A | 10/1999 | Haynes et al. | |
| 5,994,283 A | 11/1999 | Durbut et al. | |
| 6,017,417 A | 1/2000 | Wendt et al. | |
| 6,036,391 A * | 3/2000 | Holliday et al. | 401/188 R |
| D428,267 S | 7/2000 | Romano, III et al. | |
| 6,093,665 A | 7/2000 | Sayovitz et al. | |
| 6,103,061 A | 8/2000 | Anderson et al. | |
| 6,147,039 A | 11/2000 | Jacques et al. | |
| 6,156,421 A | 12/2000 | Stopper et al. | |
| 6,197,404 B1 | 3/2001 | Varona | |
| 6,200,941 B1 | 3/2001 | Strandburg et al. | |
| 6,215,038 B1 | 4/2001 | Davis et al. | |
| 6,248,125 B1 | 6/2001 | Helming | |
| 6,303,046 B1 | 10/2001 | Risen, Jr. et al. | |
| 6,303,557 B1 | 10/2001 | Colclough | |
| 6,315,864 B2 | 11/2001 | Anderson et al. | |
| 6,409,770 B1 | 6/2002 | Weiss et al. | |
| 6,432,270 B1 | 8/2002 | Liu et al. | |
| 6,508,602 B1 | 1/2003 | Gruenbacher et al. | |
| 6,588,961 B2 | 7/2003 | Lafosse-Marin et al. | |
| 6,687,942 B1 | 2/2004 | Pember | |
| 6,726,386 B1 | 4/2004 | Gruenbacher et al. | |
| 7,033,100 B2 * | 4/2006 | Barton et al. | 401/7 |
| 2003/0135181 A1 | 7/2003 | Chen et al. | |
| 2004/0053803 A1 | 3/2004 | Lye et al. | |

FOREIGN PATENT DOCUMENTS

| | | |
|---|---|---|
| EP | 0074161 A2 | 3/1983 |
| EP | 0307376 | 3/1989 |
| EP | 0369678 | 5/1990 |
| EP | 0517566 B1 | 12/1992 |
| EP | 0442292 B1 | 3/1994 |
| EP | 0603931 | 6/1994 |
| EP | 0675703 B1 | 5/1998 |
| EP | 0841049 A1 | 5/1998 |
| EP | 1046591 A2 | 10/2000 |
| EP | 1541079 A | 6/2005 |
| FR | 2602491 A | 12/1988 |
| GB | 1225713 | 3/1971 |
| JP | 55017571 | 2/1980 |
| JP | 56030869 | 3/1981 |
| JP | 58191167 | 11/1983 |
| JP | 60021255 | 2/1985 |
| JP | 62049932 | 3/1987 |
| JP | 63147652 | 6/1988 |
| JP | 02290201 | 11/1990 |
| JP | 4147863 | 5/1992 |
| JP | 5017712 | 1/1993 |
| JP | 5320549 | 12/1993 |
| JP | 7097597 | 4/1995 |
| JP | 9031378 | 2/1997 |
| JP | 10060339 | 3/1998 |
| JP | 10202910 | 8/1998 |
| WO | WO 9111105 | 8/1991 |
| WO | WO 9638548 | 12/1996 |
| WO | WO 9707729 | 3/1997 |
| WO | WO 9928411 | 6/1999 |
| WO | WO 0078861 A1 | 12/2000 |
| WO | WO 03106333 | 12/2003 |

OTHER PUBLICATIONS www.drugstore.com/templates/brand/default.asp?brand=7840, Sep. 4, 2002.

Co-pending U.S. Appl. No. 11/217,110, filed Aug. 31, 2005.

Co-pending U.S. Appl. No. 11/217,079, filed Aug. 31, 2005.

PCT Search Report, Jan. 23, 2007.

* cited by examiner

FLUID APPLICATOR WITH A PRESS ACTIVATED POUCH

BACKGROUND

Cleaning pads, wipes, and other similar devices are know that include an internal fluid containing pouch or bladder that is ruptured or otherwise breached to dispense the fluid. Typically, the pouches are designed to burst along a frangible seam or portion when pressure is applied to the device, and therefore to the pouch. The pouch is disposed adjacent a permeable cover and the fluid composition released from the pouch migrates through the permeable cover. With these products, it is generally desired to isolate the user's hand from the fluid, particularly if the fluid composition is a harsh cleaning agent or the like. For this reason, a liquid impermeable barrier layer is provided such that the pouch is contained in a space between the cover and barrier layer, with the barrier layer preventing the released fluid from contacting the user. Reference is made, for example, to the devices described in U.S. Pat. No. 6,508,602 and U.S. Pat. No. 6,588,961.

However, with conventional designs, when the fluid is released upon rupturing the pouch, it flows freely into the space between the cover and barrier layer and migrates uncontrolled through the surface area of the cover. This characteristic is not desirable in all uses of the devices. For example, it may be desired to concentrate the fluid composition at only a selected area of the cover, for example at the longitudinal end of the device where it can be applied by the user's fingers. Migration of the fluid composition elsewhere through the cover can be wasteful and otherwise undesirable.

SUMMARY

Objects and advantages of the invention will be set forth below in the following description, or may be obvious from the description, or may be learned through practice of the invention.

As noted, many cleaning devices and other similar products utilizing internal pouches to deliver a fluid composition are deficient in that migration of the fluid through the cover material is generally uncontrolled. The present invention relates to a fluid applicator that allows for a focused and concentrated application of the fluid composition released from an internal pouch.

The present disclosure is directed generally to a fluid applicator device, such as a pad, mitt that may be worn on a user's hand or fingers, or other suitable structure, intended to deliver a fluid composition from a pouch contained within the device. For ease of description only, aspects of the invention are explained herein by reference to cleaning pad, wipes, and mitt embodiments used to deliver any desired cleaning agent or composition contained within the internal pouch. However, it should be appreciated that the invention is not limited to such devices, and includes all embodiments of pads, wipes, mitts, hand wipes, or any other fluid applicator incorporating the novel aspects of the invention.

The fluid applicator may be a disposable, absorbent or non-absorbent article. In a particular embodiment, the product is configured as a cleaning mitt designed to fit onto a user's hand or multiple fingers. Such a mitt may be used, for example, to apply a cleaning agent or composition to a surface. The mitt may also be used for cleaning the surface with the composition. The mitt can be used to clean various utensils, objects or surfaces, and to polish various items with any number of compositions or agents carried by the wipe. For example, in one embodiment, the mitt can be used to polish silver with a polish contained in the pouch. The mitt may also be used to clean or treat parts of the body, or to apply a medicine, lotion, ointment, cleaning agent, or the like to any part of the body, or any other object. All such uses of a fluid applicator are contemplated within the scope and spirit of the invention.

In an alternate embodiment, the fluid applicator is configured as a pad or "pillow" like structure designed to be held or grasped by a user, with the fluid composition pouch contained within the pad.

In still another embodiment, the fluid applicator may be a wipe defined by a single substrate with the unique pouch configuration attached to one side of the substrate, as described below.

In a particular embodiment, the fluid applicator includes a cover layer, and a back layer attached to the cover layer to define an interior space therebetween. A pouch is disposed within the interior space, and a fluid composition is contained within the pouch. A rupturable seal is configured at a location on the pouch that is adjacent the cover layer. The seal is designed to rupture or burst upon a user applying pressure to the pouch. A circumferential barrier is defined around the seal and is disposed between the cover layer and the pouch material in which the seal is formed. The barrier is sealed to the underside of the cover layer and, in this manner, circumscribes a portion of the cover layer. At least one exit passage is defined through the cover layer within the circumscribed portion such that the fluid composition released upon rupture of the pouch seal migrates only through the circumscribed portion of the cover layer.

To define a mitt, the back layer and cover layer may be attached so as to define a closed end structure with an opening between the respective layers through which a user may insert their hand or fingers.

For a pad construction, the back layer and cover layer may be bonded together around the complete circumference of the device, with the pouch sandwiched between the layers.

In a wipe construction, the back layer may be eliminated and the pouch is exposed and simply attached directly to the back side of the cover layer.

The circumscribed portion may be defined at any desired location on the cover layer. In a mitt embodiment, it may be desired to define the circumscribed portion near the closed end of the applicator where the fluid composition may be applied by the user's fingers.

The barrier may be defined by an adhesive bead that is deposited in a closed loop around the rupturable pouch seal. The shape of the loop thus defines the geometry and surface area of the defined application portion of the cover layer. The adhesive bead attaches to the pouch and to the cover layer so as to define an enclosed barrier for the fluid composition.

In an embodiment wherein the cover layer is a fluid impermeable material, the exit passage in the cover layer may comprise any manner of opening, holes, apertures, slits, and so forth, defined in the material. If the cover layer is a fluid permeable material, the exit passage may be defined by the permeable nature of the material alone or in combination with additional exit passage structure.

The cover layer may include a textured outer face to enhance the cleaning or scrubbing effect of the applicator. At least one of the cover layer or back layer may be an elastomeric material to give the applicator form-fitting characteristics when used as a mitt.

To prevent inadvertent release of the fluid composition during shipping, handling, storing, and so forth, it may be desired to include a removable seal over the exit passage in the cover layer. This seal may be a tab releasably attached to the cover layer with an appropriate adhesive. In alternate embodiments, this seal may be the primary seal such that the rupturable seal in the pouch is eliminated. In other words, the pouch is open to the cover layer within the circumscribed portion, with the tab seal on the exterior of the cover layer preventing release of the fluid composition through the cover layer.

Aspects of the invention are set forth in greater detail below by reference to embodiments illustrated in the figures.

DETAILED DESCRIPTION OF THE PREFERRED EMBODIMENTS

Figure 1A:
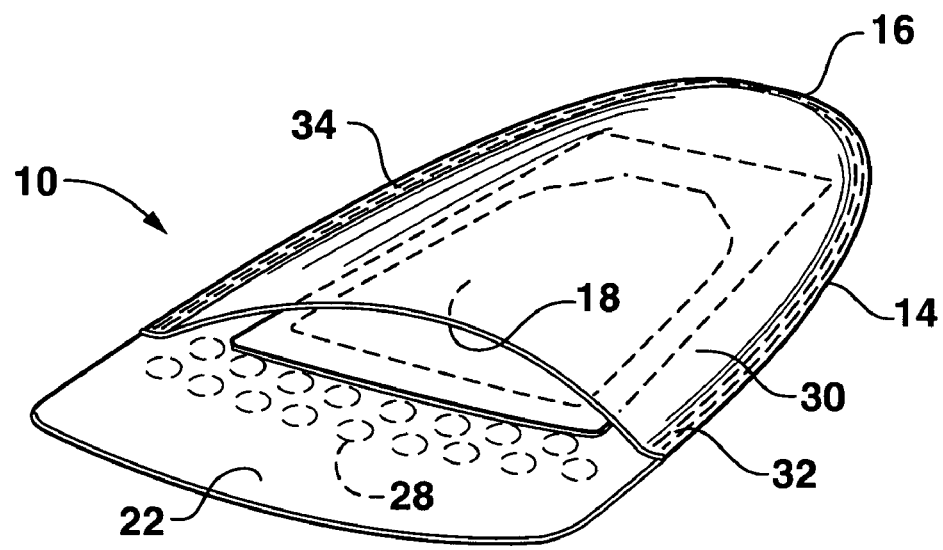
FIG. 1A is a perspective back view of a mitt embodiment of the invention.

Reference will now be made in detail to one or more embodiments of the invention, examples of which are illustrated in the drawings. The embodiments are provided by way of explanation of the invention, and are not meant as a limitation of the invention. Features illustrated or described as part of one embodiment may be used with another embodiment to yield still a different embodiment. It is thus intended that the present invention include modifications and variations to the embodiments illustrated and described herein.

Aspects of the invention are described herein by reference to cleaning mitt, pad, and wipe devices. It should be appreciated that the invention is not limited to such devices, and is applicable to any applicator intended to deliver a fluid composition from an internal pouch for any purpose.

Figure 2:
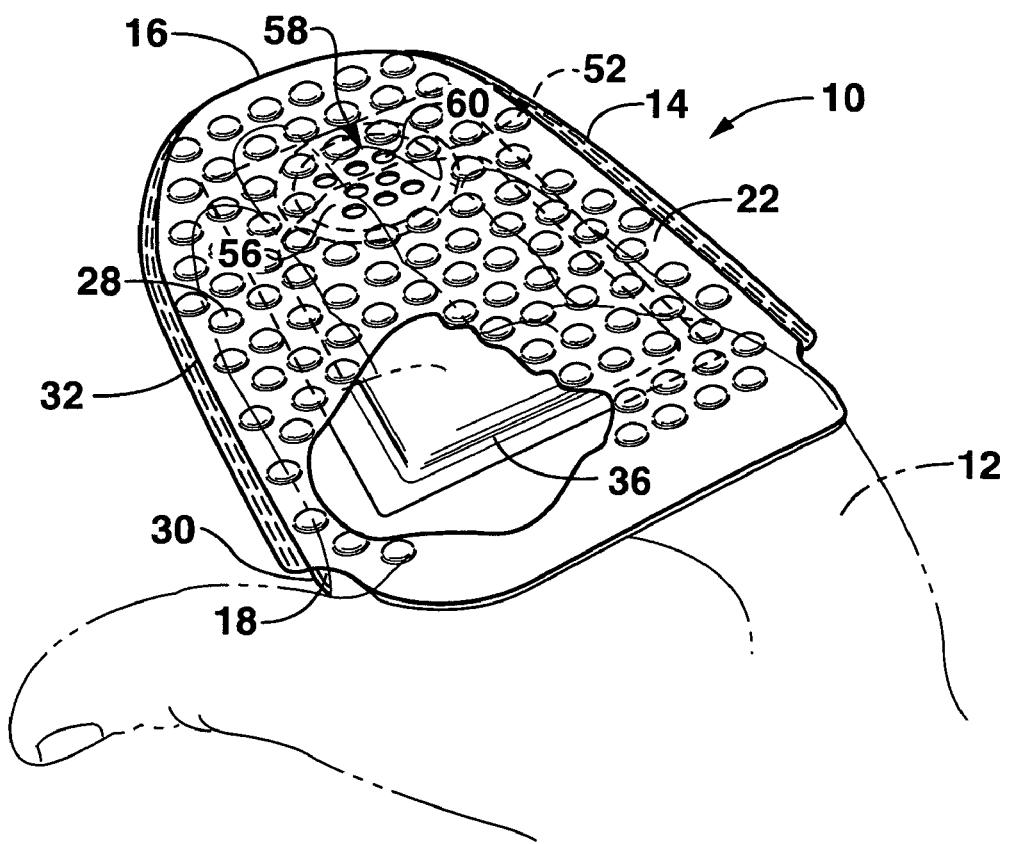
FIG. 2 is a perspective and partial cut-away view of a mitt embodiment taken from the cover layer side.

Referring to the figures in general, various embodiments of an applicator 10 are illustrated. In FIG. 1A, the applicator 10 is configured as a mitt structure 14 that fits onto a user's hand or fingers 12, as illustrated in FIG. 2. The mitt structure has a closed end 16 and an opening 18 at the opposite longitudinal end through which a user inserts their hand 12 or fingers. The applicator 10 is designed to deliver a fluid composition 38 from a pouch 36 contained within the mitt when the user presses the applicator against a surface, or otherwise applies pressure to the pouch 36. The fluid composition 38 is delivered only through a defined circumscribed portion 56 of a cover layer 22, as described in greater detail below.

Figure 1B:
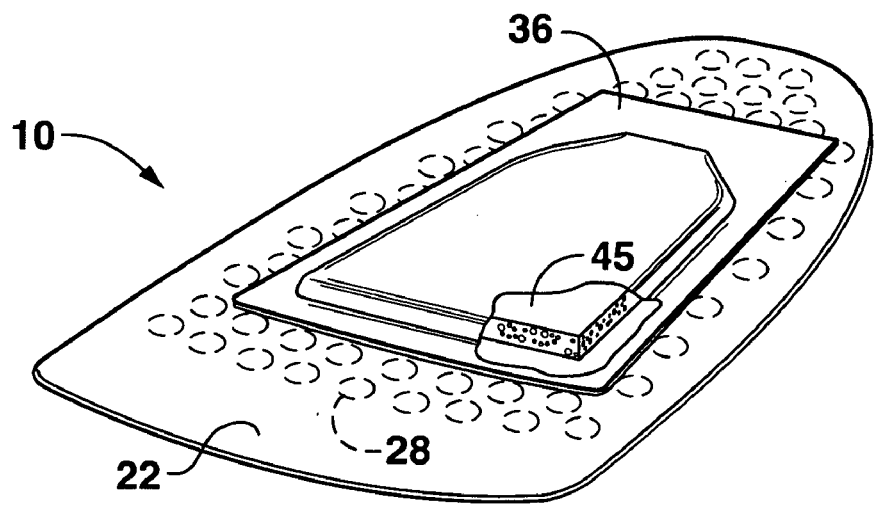
FIG. 1B is a perspective back view of a pad embodiment of the invention.

In the embodiment of FIG. 1B, the applicator 10 is configured as a wipe having a single substrate cover layer 22 with the pouch 36 attached directly to the back side of the layer 22. The opposite side of the cover layer 22 constitutes an application side of the layer 22. The pouch remains completely exposed in use of this embodiment.

Figure 1C:
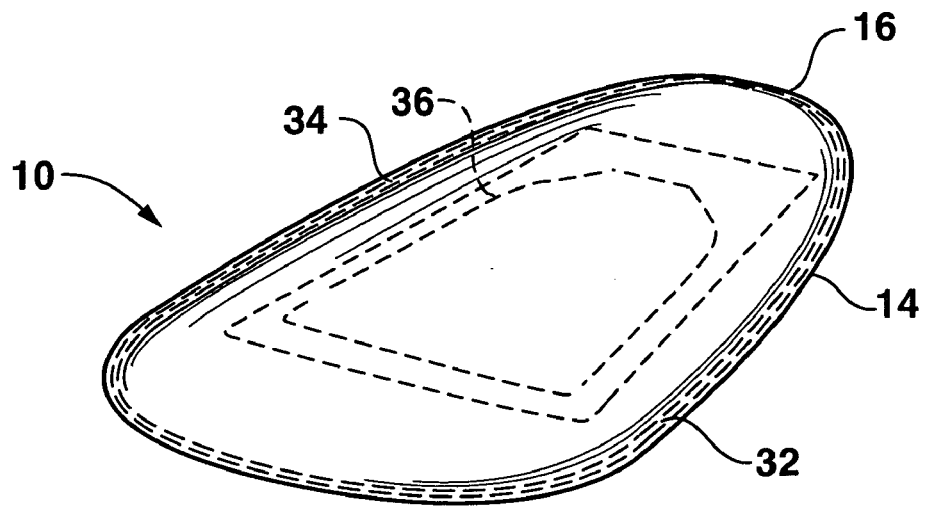
FIG. 1C is a perspective back view of a wipe embodiment of the invention.

In the embodiment of FIG. 1C, the applicator 10 is configured as a pad wherein the cover layer 22 and back layer 30 form a closed pillow-like structure with the pouch 36 disposed between the layers 22, 30.

It should be appreciated that the invention is not limited to any particular type of fluid composition 38 or intended use of the applicator 10. The fluid composition 38 may be any flowable substance, including powder and granular substances.

In certain embodiments, the applicator 10 includes the cover layer 22 attached to a back layer 30 around a perimeter seam 32 of weld points 34 to form the mitt structure 14 with opening 18 between the cover layer 22 and back layer 30, as in FIGS. 1A and 2. For an embodiment wherein the applicator 10 is configured as a pad, the seam 32 is continuous around the perimeter without an opening for a hand, as in FIG. 1C. In these embodiments, the application side of the cover layer 22 faces outward, and the back side of the cover layer 22 faces the back layer 30.

The pouch 36 is disposed in the interior space between the cover layer 22 and back layer 30 in the mitt and pad embodiments. With the mitt embodiment, the cover layer 22 may be liquid impermeable, and the user's hand may be in direct contact with the pouch 36 without a liquid impermeable barrier layer separating the hand from the pouch 36. In an alternate embodiment wherein the cover layer 22 is liquid permeable, it may be desired to include a barrier layer, such as a liquid impermeable film, to isolate the pouch 36 from the user's hand. This barrier layer may be a polyolefin-type material that can be heat sealed or ultrasonically sealed with the cover layer 22 and back layer 30. With this arrangement, the pouch 36 is located between the barrier layer and the cover layer 22. The various layers may be attached by any conventional bonding method suitable for the selected materials, including adhesives, thermal bonding, ultrasonic bonding, welding, stitching, and so forth. In one aspect of the present invention, the cover and back layers 22, 30 are attached using a block copolymer adhesive such as 34-5610 construction adhesive available from National Starch. The cover and base layers 22, 30 may also be attached at locations in addition to or other than the perimeter seam 32.

Figure 3:
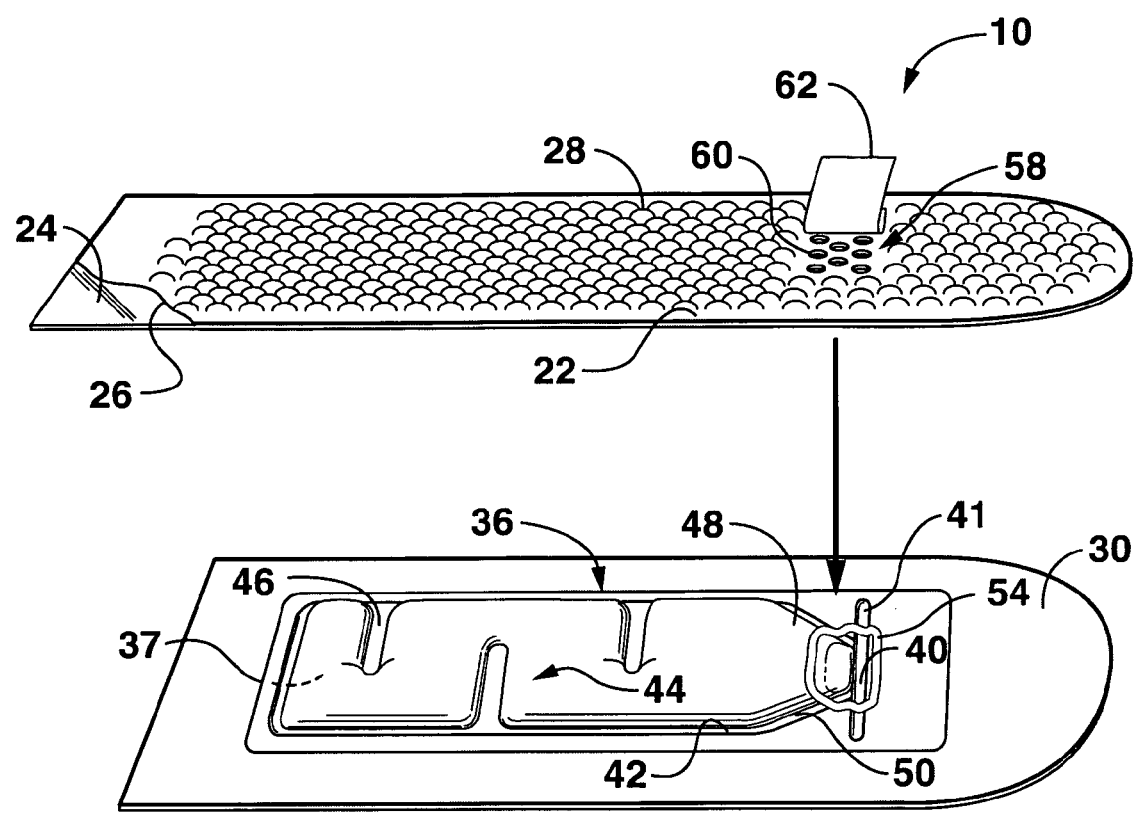
FIG. 3 is a component view of a mitt embodiment particularly illustrating the pouch and barrier structure.

The cover layer 22 is an active layer used to deliver the fluid composition 38 and perform the cleaning function. Any number or combination of suitable materials may be used for the cover layer 22. In a particular embodiment, the cover layer 22 is a laminate of a liquid impermeable film 24 and a woven or nonwoven web 26, as depicted in FIG. 3. The cover layer may include an absorbent material. The cover layer 22 may be a stretch-bonded laminate (SBL) with pre-stretched elastic filament and meltblown material with one ply of spunbond material on each outer surface and a basis weight of approximately 70 gsm, but any suitable absorbent material may be used. SBL and other composite nonwoven elastic webs are further described in U.S. Pat. No. 4,657,802 to Morman. In one aspect of the present invention, the cover layer 22 includes a dry embossed 110 grams per square meter (gsm) coform laminate available from Kimberly-Clark Corporation.

In other aspects of the present invention, materials for the cover layer 22 may include cotton, rayon, wood pulp, and polymeric substances such as nonwoven fabrics, foam sponges, and thermoplastics. The material may be formed of a nonwoven fabric that is made of interbonded thermoplastic fibers. The fibers may be formed from a variety of thermoplastic materials including polyolefins (e.g., polyethylene or polypropylene), polystyrene, and polyamides (e.g., nylon). In addition, thermoplastic polymers that are elastomeric may also be used as fibers, including polyurethanes and block copolymers. Blends of any of these materials may be used to form the fibers. The fibers may include additives (e.g., wax, pigments, stabilizers, and fillers) that are inserted as the fibers are fabricated to achieve one or more desired properties within the fibers. Some example additives include compatible surfactants that are added to the polymers to make the surface of the fibers more wettable, thereby improving the ability of the fiber structure to attract unwanted debris away from the skin. The amount of surfactant added to the fibers can be adjusted to control the surface wetting of the fabric formed from the fibers. Examples of suitable surfactants include sodium dioctyl sulfosuccinate and alkyl phenoxy ethanol.

Material used in making the cover layer 22 may be capable of capturing and/or storing substances within the material. Such material may store and/or capture debris, cleansers, lubricants, spermicidal agents, and medications, among other materials, before or while using the applicator 10. Examples of such materials include spunbond, spunlace, bonded carded web, and apertured film materials. In one aspect of the present invention, the material is an apertured film that is formed of a polyolefin that may be combined with a nonwoven fabric. In other aspects of the present invention, the cover layer material may be a laminate of like, similar, or different tissue, nonwoven, woven, or film materials, or of any other materials described herein.

When a nonwoven fabric is used, the basis weight of the nonwoven fabric may vary depending on the properties that are desired within the applicator 10. As an example, the basis weight for the nonwoven fabric may be as low as 10 gsm and as high as 300 gsm. Such nonwoven materials may include a textured surface. Examples of such nonwoven textured materials include rush transfer materials, flocked materials, wireform nonwovens, and thermal point unbonded materials, among others.

The back layer 30 is preferably of the same general size and shape as the cover layer 22, although this is not a requirement, and may be made from the same material as the cover layer 22, or a different material. In an embodiment not illustrated in the figures, the back layer 30 and cover layer 22 may be formed from a folded piece of the same material, with the fold defining the closed end of the mitt structure 14, or a closed end of a pad structure. The back layer 30 may be a single or multi-layer film, or a laminate of a nonwoven material and a film. In another aspect, the back layer may be a material such as BSTL, a breathable, stretchable, thermal laminate. BSTL and similar materials are described in U.S. Pat. No. 5,695,868 to McCormack et al. and U.S. pat. No. 5,843,056 to Good et al. In yet another aspect of the present invention, the back layer may be SBL as described above, or may be any other suitable material, particularly those described above with reference to the cover layer 22.

In certain embodiments, for example cleaning pad applicators, it may be desired that the back layer 30 is also an active layer. In this regard, the back layer 30 may be made of any one or combination of the materials described above as suitable for the cover layer 22.

When the applicator 10 is used to scrub or clean surfaces, or in dental applications as a finger wipe, the active surfaces may include a texturized surface. The manner in which a texturized surface is formed on a nonwoven web for use in the present invention can vary depending upon the particular application of the desired result. The active surfaces may be made from a nonwoven web that has been thermally point unbonded to form a plurality of tufts. As used herein, a substrate that has been "thermally point unbonded " refers to a substrate that includes raised unbonded areas or lightly bonded areas that are surrounded by bonded regions. For example, as shown in the figures, bumps or tufts 28 are the unbonded or lightly bonded areas that form raised projections off the surface of the nonwoven web to provide the necessary texture.

The material used for the point unbonding process can vary depending upon the particular application. For instance, the material can be a single layer or can include multiple layers of material. For most applications, the total basis weight of the material should be at least 1 osy, and particularly from about 3 osy to about 9 osy. Higher basis weights are needed in order to produce tufts with an appropriate height.

Besides point unbonded materials, there are many other methods for creating texturized surfaces on base webs and many other texturized materials can be utilized.

Examples of known nonwoven, texturized materials, include rush transfer materials, flocked materials, wireformed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured conform materials. In general, "conform" means a process in which at least one meltblown diehead is arranged near a chute through which other materials are added to the web while it forms. Such other materials can include, for example, pulp, superabsorbent particles, or cellulose or staple fibers. Coform processes are described in U.S. Patent No. 4,818,464 to Lau and U.S. pat. No. 4,100,324 to Anderson, et al. Webs produced by the coform process are generally referred to as coform materials.

In one embodiment, the texturized material can be a loop material. As used herein, a loop material refers to a material that has a surface that is at least partially covered by looped bristles that can vary in height and stiffness depending upon the particular application. Further, the looped bristles can be sparsely spaced apart or can be densely packed together. The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

For mitt embodiments of the applicator 10, it may be desired for the back layer 30 to be an elastomeric material so as to provide the mitt structure with form-fitting characteristics.

By virtues of the design and materials chosen for the applicator 10, the applicator is preferably designed to be disposable. In this case, disposable means that the device 10 is disposed of, rather than cleaned, after use.

As seen in various figures, the pouch 36 contained within the applicator 10 defines a cavity 37 (FIG. 3) in which the fluid composition 38 is contained. The pouch may be formed from opposed layers of material attached together to define the sealed cavity, as seen for example in FIG. 3. The opposed layers may be attached by thermal bonding, although any suitable attachment method may be used depending on the type of material selected for the layers.

The pouch 36 may be made from a flexible, heat sealable material such as 2 mil polyethylene film available from Bemis Company, Inc. In other aspects of the present invention, the pouch 36 may be made from polyethylene, polypropylene, or other suitable thermoplastics, or metalized films. The material from which the pouch 36 is made should have no negative impact on or reaction with the fluid composition 38 contained in the pouch. The materials used in the construction of the pouch 36 and the fill level of the fluid composition 38 within the pouch 36 create a structure that is durable and flexible, and one that is not easily burst open during normal handling. It may be desired to attach the pouch 36 to one or both of the cover layer 22 and back layer 30.

In one aspect of the present invention, the pouch 36 may also include one or more bonding points or seals 42 at which the opposed pouch layers are bonded to each other to define a cavity or other features of the pouch 36. For example, referring to FIG. 3, the pouch 36 includes bond lines 46 that define baffles within the cavity, the baffles serving to control flow rate of the fluid composition from the pouch. Additional bond lines 50 define a nozzle 48.

In the embodiment of FIG. 1B, a sponge 45 or other suitable absorbent web material is disposed within the pouch 36 as a means to control flow rate of the fluid composition 38 from the pouch 36. The fluid composition is absorbed by the sponge 45 and is expelled as a function of pressure applied to the pouch 36, and thus to the sponge 45.

Exit structure 40 is provided in one of the layers of the pouch 36 through which the fluid composition 38 flows in use of the applicator 10. Configuration of the exit structure 40 can vary. For example, the structure 40 may comprise any pattern of holes, slits, apertures, or other openings defined completely through the respective pouch layer. In alternate embodiments, the exit structure 40 may be weakened positions in the pouch material or seam structure designed to rupture or burst upon pressure being exerted on the pouch.

In particular embodiments, the exit structure 40 includes a rupturable or burstable seal that is configured at a location on the pouch 36 adjacent to the cover layer 22. The seal is designed to release or rupture upon a user applying pressure to the pouch 36. In the illustrated embodiment, the seal is defined by a bond line 41 that is weaker than the bonds 42 used to define the cavity between opposed layers of the pouch 36, as well the baffle and nozzle bonds 46, 50. In alternate embodiments, the bond line 41 may be a scored line, frangible seal, thinned portion of the pouch material, or any other suitable configuration that will open or separate upon pressure being applied to the pouch 36. The side of the pouch 36 containing the seal 40 is disposed adjacent to the cover layer material 22.

A circumferential barrier 52 is defined around the seal 40 and is disposed between the cover layer 22 and the pouch 36. The barrier 52 generally surrounds the seal 40 in the pouch 36 and is sealed to the underside of the cover layer 22. In this manner, the barrier 52 circumscribes a portion of the cover layer 22 that is in communication with the underlying seal 40. This circumscribed portion 56 may be defined at any desired location on the cover layer 22. For example, in a mitt embodiment, the circumscribed portion 56 may be defined near the closed end 16 of the mitt structure 14 where the fluid composition may be applied by the user's fingers.

The barrier 52 may be defined by various methods. In a particular embodiment, the barrier 52 is defined by an adhesive bead 54 that is deposited in a closed loop pattern around the rupturable seal 40. The shape of the loop defines the geometry and surface area of the circumscribed portion 56 of the cover layer 22. The adhesive bead 54 attaches to the pouch 36 and to the underside of the cover layer 22 so as to essentially define an enclosed barrier for the fluid composition 38 that is released through the rupturable seal 40 upon pressure being applied to the pouch 36.

At least one exit passage, generally 58, is defined through the cover layer 22 within the circumscribed portion 56. The fluid composition 38 that is released upon rupture of the pouch seal 40 migrates through the exit passage. Thus, it should be understood that the fluid composition 38 migrates only through the portion of the cover layer 22 within the circumscribed portion 56. In this way, the amount and delivery location of the fluid composition 38 is concentrated and focused at only one location on the cover layer 22 depending on the location of the circumscribed portion 56.

The exit passage 58 may be defined as any manner of opening or holes 60, as illustrated in FIGS. 2 and 3, or any other suitable aperture, slits, or openings of any sort defined through the cover layer 22. In the embodiment wherein the cover layer 22 is a fluid permeable material, the exit passage may be provided simply by the permeable nature of the material alone. In other words, it is not necessary to define additional holes or openings through the material. The size, number, and pattern of the exit passages 58 may vary depending on the viscosity of the fluid composition 38 and desired flow rate of the composition through the cover layer 22.

Figure 4A:
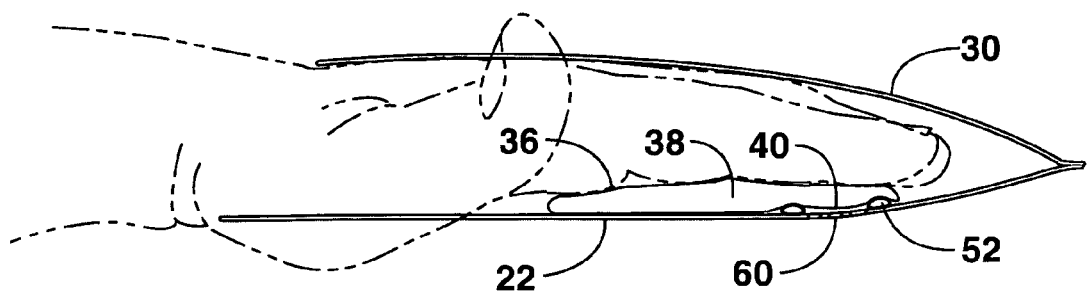
FIGS. 4A and 4B are cross-sectional views of an embodiment of a pouch shown prior to activation in FIG. 4A and after activation in FIG. 4B.
Figure 4B:
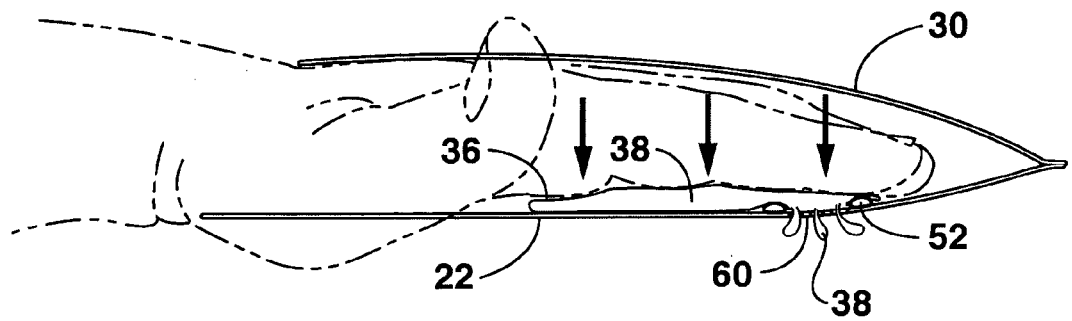

An exemplary embodiment is illustrated in the cross-sectional view of FIG. 4A prior to being activated by the user. This embodiment illustrates a mitt embodiment wherein a user inserts their hand into the device, with the hand being in direct contact with the pouch 36, as illustrated in FIG. 4B. To activate the pouch 36, the user would press the cover layer 22 against a surface, thereby applying pressure to the pouch 36. Alternatively, the user may simply grasp and squeeze the pouch 36. The pressure exerted on the pouch 36 causes the seal 40 to rupture or separate and the fluid composition 38 is delivered through the opened seal 40 and through the exit holes 60 or other passages within the circumscribed area of the cover layer 22 bordered by the adhesive barrier 52. The barrier 52 prevents the fluid composition 38 from migrating to other areas of the cover layer 22 prior to being forced through the cover layer. The barrier 52 also prevents the fluid composition 38 from migrating into the interior space between the cover layer 22 and back layer 30. If the cover layer 22 is an otherwise fluid impermeable material, the user's hand is thus protected from contact with the fluid composition 38 without the need of an additional fluid impermeable barrier layer between the pouch 36 and the user's hand.

To prevent inadvertent release of the fluid composition 38 during shipping, handling, storage, and so forth, it may be desired to include a removable seal tab 62 attached to the outer surface of the cover layer 22 over the exit passage holes 60, as illustrated in FIG. 3. This seal 62 may be any conventional fluid impermeable material that is releasably sealed to the cover layer with an appropriate releasable adhesive.

In an alternate embodiment, pouch may be open within the circumscribed portion 56 such that the seal tab 62 is the only seal preventing flow of the fluid composition from the pouch 36. In this embodiment, the rupturable seal 40 is thus eliminated. This embodiment may be useful for less viscous fluid compositions, including powders and granular materials.

As mentioned, the fluid composition 38 contained within the pouch 36 may be any fluid suitable for the intended use of the applicator 10, including cleansing fluids for human/animal use and cleaning fluids for cleaning surfaces. The fluid may be any paste, gel, powder, oil, liquid, or any other appropriate medium. Example cleansing fluids include surfactants such as water-soluble polymers, polysorbates, glycerins, glycol-based surfactants, and/or silicone-based surfactants. The fluid may include other materials, such as water, salts, vinegars, humectants, scouring powders, thickening agents, and fragrances. A cleansing fluid may also include a moisturizer that helps to maintain a normal skin hydration level. A cleansing fluid may also include preservatives and other ingredients that do not disrupt the normal flora of the vaginal area (e.g., sorbic acid, citric acid, methyl paraben, and natural preservatives such as grapefruit extract). The fluid may include other materials that may be applied to an area of the body. Example materials include lubricants, deodorants, and other inactive or active ingredients (e.g., spermicidal agent or medication). In one aspect of the present invention, the fluid is a cleansing fluid that is primarily a water-based solution (90%+water content) with a surfactant, preservatives, pH neutralizers, and a thickening agent.

The fluid may be a cleaning solution such as FOUR PAWS Super Strength Stain and Odor Remover, which includes water, natural enzymes, and mild detergent (from Four Paws Products, Ltd., Hauppauge, N.Y.), or NATURE'S MIRACLE Stain & Odor Remover, which includes water, natural enzymes, isopropyl alcohol, and natural citrus scent (from Pets 'N People, Inc., Rolling Hills Estates, Calif.), or RESOLVE Carpet Spot & Stain Carpet Cleaner (from Reckitt Benckiser, Wayne, N.J.). The fluid may be a pet shampoo. The fluid may be a stain cleaner and stain guard such as SCOTCHGARD Oxy Carpet Cleaner with Stain Protector that includes water, 2-butoxyethanol, hydrogen peroxide, and surfactants (from 3M Corporation, St. Paul, Minn.). In the case of using the cleaning device 10 to clean a fabric surface, the fluid may include a pet repellant such as SIMPLE SOLUTION Indoor/Outdoor Repellent for Dogs and Cats, which has as an active ingredient methyl nonyl ketone (from The Bramton Company, Dallas, Tex.).

The fluid may be an antimicrobial. Examples of suitable antimicrobials include quaternary ammonium compounds such as 3-trimethoxysilylpropyidimethyloctadecyl ammonium chloride (AEGIS); poly cationic chemicals such as biguanides ( poly (hexamethylene) biguanide hydrochloride (PHMB) Arch Chemical), 2, 4, 4'-Trichloro-2'- hydroxyldipenylether (Tinosan, Ciba); diphenyl ether (bis-phenyl) derivatives known as either 2, 4, 4'-trichloro-2' hydroxy dipenyl ether or 5-chloro-2-(2, 4-dichlorophenoxyl) phenol; triclosan; silver; and copper. The fluid may be an allergen sequestrant that may be a charged or mixed charged particle or nanoparticle. Most allergy proteins are glycoproteins (proteins that contain covalently-bound oligosaccharides), so a negative charge may be better then predominance of positive charges on the particles, although mixed charges may be preferred. Clays or modified clays work in this respect. Examples of suitable allergen sequestrants include plant lectins with an affinity for N-acetylgalactosamine such as jacalin, peanut, and soybean, where the lectins both bind allergens and are bound to the web, thus removing allergens from a surface. The fluid may also include a fragrance. The fluid may also include a pheromone to either attract or repel an animal. The fluid may also be shoe polish, a carpet cleaning solution, a stain removal fluid, kitchen floor and counter top cleaners, etc.

Embodiments of the invention have been described with reference to various specific and illustrative aspects and techniques. However, it should be understood that many variations and modifications may be made while remaining within the spirit and scope. Accordingly, this is intended to embrace all such alternatives, modifications and variations that fall within the spirit and scope of the appended claims.

What is claimed is:

1. A fluid applicator device, comprising:
    a cover layer having an application side and an opposite back side;
    a self-contained fluid impermeable pouch formed separate from said cover layer and positioned against said back side of said cover layer, and a fluid composition contained within said pouch;
    exit structure configured at a location on said pouch, said pouch disposed such that said exit structure is facing said back side of said cover layer;
    a circumferential barrier defined around said exit structure and disposed between said back side of said cover layer and said pouch, said barrier circumscribing a portion of said cover layer and a portion of said pouch such that said pouch extends beyond said circumferential barrier; and
    at least one exit passage defined through said cover layer within said circumscribed portion such that fluid composition released from said exit structure migrates through said circumscribed portion of said cover layer to said application side of said cover layer.

2. The fluid applicator as in claim 1, wherein said barrier comprises an adhesive bead deposited in a closed loop around said exit structure.

3. The fluid applicator as in claim 2, wherein said adhesive bead attaches said pouch to said cover layer.

4. The fluid applicator as in claim 1, wherein said exit passage comprises at least one hole defined through said cover layer.

5. The fluid applicator as in claim 1, wherein said cover layer comprises a liquid impermeable material.

6. The fluid applicator as in claim 1, wherein said cover layer comprises a textured outer face.

7. The fluid applicator as in claim 1, wherein said cover layer comprises a laminate of a liquid impermeable material and a nonwoven material 8. The fluid applicator as in claim 1, further comprising a back layer attached to said cover layer to form an interior space therebetween, said pouch disposed within said interior space.

9. The fluid applicator as in claim 8, wherein said back layer and said cover layer define a miff structure with an opening for insertion of a user's hand or fingers.

10. The fluid applicator as in claim 9, wherein said back layer comprises an elastomeric material.

11. The fluid applicator as in claim 9, wherein said circumscribed portion of said cover layer is adjacent a closed longitudinal end of said mitt structure.

12. The fluid applicator as in claim 9, wherein said cover layer comprises a liquid permeable material, and further comprising a liquid impermeable barrier layer disposed within said interior space between said pouch and said back layer.

13. The fluid applicator as in claim 8, wherein said back layer and said cover layer define a closed pad structure.

14. The fluid applicator as in claim 1, wherein said device is configured as a cleaning device and said fluid composition comprises a cleaning agent.

15. The fluid applicator as in claim 1, further comprising baffles within said pouch.

16. The fluid applicator as in claim 15, wherein said baffles comprise seal lines between opposed layers of said pouch.

17. The fluid applicator as in claim 1, further comprising an absorbent body contained within said pouch.

18. A fluid applicator device, comprising:
    a cover layer having an application side and an opposite back side;

a self-contained pouch positioned against said back side of said cover layer, and a fluid composition contained within said pouch;

exit structure configured at a location on said pouch, said pouch disposed such that said exit structure faces said back side of said cover layer;

a circumferential barrier defined around said exit structure and disposed between said cover layer and said pouch, said barrier circumscribing a portion of said cover layer and a portion of said pouch such that said pouch extends beyond said circumferential barrier;

at least one exit passage defined through said cover layer within said circumscribed portion such that fluid composition released from said exit structure migrates through said circumscribed portion of said cover layer to said application side of said cover layer; and wherein said exit structure in said pouch comprises a rupturable seal in said pouch that is opened upon sufficient pressure being applied to said pouch.

19. A fluid applicator, comprising:

a cover layer attached to a back layer so as to define an interior space therebetween, said cover layer having an application side and a back side;

an internal self-contained pouch disposed within said interior space against said back side of said cover layer, said pouch containing a fluid composition;

a rupturable seal configured at a location on said pouch, said pouch disposed within said interior space such that said seal faces said back side of said cover layer; and said seal in isolated fluid communication with a defined portion of said cover layer that is permeable to said fluid composition within said defined portion such that fluid composition released from said rupturable seal migrates through said cover layer to said application side of said cover layer only within said defined portion; and wherein the defined portion of the cover layer circumscribes a portion of said pouch such that said pouch extends beyond said circumferential barrier.

20. The fluid applicator as in claim 19, comprising a barrier between said pouch and said cover layer that circumscribes said defined portion.

21. The fluid applicator as in claim 20, wherein said barrier comprises an adhesive bead.

22. The fluid applicator as in claim 21, wherein said adhesive bead attaches said pouch to said cover layer.

23. The fluid applicator as in claim 19, wherein said cover layer comprises a liquid impermeable material, and further comprising at least one passage hole defined through said cover layer within said defined portion through which said fluid composition migrates.

24. The fluid applicator as in claim 23, wherein said cover layer comprises a laminate of a liquid impermeable material and a nonwoven material.

25. The fluid applicator as in claim 19, wherein said back layer comprises an elastomeric material.

26. The fluid applicator as in claim 19, wherein said cover layer and said back layer define a mitt structure having a closed longitudinal end and an open end for insertion of a user's hand or fingers into said interior space, said defined portion of said cover layer adjacent said closed longitudinal end of said mitt structure.

27. The fluid applicator as in claim 19, wherein said cover layer and said back layer define a closed pad structure.

28. The fluid applicator as in claim 19, further comprising a removable seal tab attached to an outer application face of said cover layer over said defined portion.

29. The fluid applicator as in claim 19, wherein said cover layer comprises a liquid permeable material, and further comprising a liquid impermeable barrier layer within said interior space between said pouch and said back layer.

* * * * *

UNITED STATES PATENT AND TRADEMARK OFFICE
CERTIFICATE OF CORRECTION

PATENT NO. : 7,604,623 B2
APPLICATION NO. : 11/215816
DATED : October 20, 2009
INVENTOR(S) : Brunner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this

Fifth Day of October, 2010

David J. Kappos
*Director of the United States Patent and Trademark Office*